US00PP08428P

United States Patent [19]

Jessel, Jr.

[11] Patent Number: Plant 8,428

[45] Date of Patent: Oct. 19, 1993

[54] CARNATION PLANT NAMED CFPC SARABANDE

[75] Inventor: Walter H. Jessel, Jr., Salinas, Calif.

[73] Assignee: California Florida Plant Co., L.P., Salinas, Calif.

[21] Appl. No.: 950,468

[22] Filed: Sep. 24, 1992

[51] Int. Cl.[5] ..... A01H 5/00

[52] U.S. Cl. ..... Plt./70.7

[58] Field of Search ..... Plt./70.7, 73.1

*Primary Examiner*—Howard J. Locker

*Attorney, Agent, or Firm*—Christie, Parker & Hale

[57] ABSTRACT

A new carnation of dark red coloration.

1 Drawing Sheet

SUMMARY OF THE INVENTION

The present invention relates to a new and distinct variety of carnation plant which was originated by me in a controlled breeding program by my crossing as seed parent the variety known as 'Rony' and as male parent the variety known as 'CFPC Sabre', (U.S. Plant Pat. No. 7,483). The varietal denomination of this new carnation is 'CFPC Sarabande'.

Among the novel combination of characteristics possessed by the new variety which distinguishes it are strong plants producing flowers of attractive dark red flower coloring in sprays and which do not show anthers at maturity. The new variety has more petalage than either of its parent and roots well with very little loss.

Asexual reproduction by propagation by side shoot cuttings of the new variety as performed in Salinas, Calif., shows that the foregoing and other distinguising characteristics come true to form and are established and transmitted through succeeding propagations. Although propagation by side shoot cuttings is described, other known methods of asexual reproduction may also be used to reproduce 'CFPC Sarabande'.

BRIEF DESCRIPTION OF THE ILLUSTRATION

The accompanying illustration shows typical specimens of the vegetative growth and flowers in different stages of development of the new variety depicted in color as nearly true as it is reasonably possible to make the same in a color illustration of this character.

DESCRIPTION OF THE NEW VARIETY

The following is a detailed description of my new variety, which color terminology in accordance with the Royal Horticultural Society Colour Chart (R.H.S.C.C.). The terminology used in the color description herein refers to plate numbers in the aforementioned color chart. Color designations and color descriptions may deviate from the stated values depending upon varying envirnomental, seasonal and cultural conditions.

The information provided herein is based on observations of plants grown inside commercial greenhouses at Fremont, Calif. The height of plant and flower and foliage size are established as an average using standard commercial cultural practices.

Name: 'CFPC Sarabande'.

Classification:

*Botanical.*—*Dianthus caryophyllus.*

*Commercial.*—Carnation, spray type.

Parentage:

*Female parent.*—'Rony'.

*Male parent.*—'CFPC Sabre'.

Plant:

*Height.*—About 24 inches.

*Growing habit.*—Herbaceous, semi-upright.

*Blooming habit.*—Terminal as a spray.

*Blooming season.*—Year round.

*Rooting time.*—About 14 days.

*Mutation prone.*—Does not appear to be.

*Disease resistance.*—Unknown to date but superior to date than 'CFPC Sabre'.

*Breaking action.*—Good.

Foliage:

*Color.*—Upper side: Near 135A. Lower side: Near 135B.

*Size.*—About 5½ inches long at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About 1½ inches.

*Diameter.*—About 1½ inches.

Calyx:

*Number of sepals.*—About 5.

*Length.*—About 1-inch.

*Width.*—About ⅓-inch.

*Color.*—Outside — near 143B. Inside — near 145C.

Bloom:

*Shape.*—Round.

*Size.*—Diameter average: About 2⅓ inches. Depth average: About 1½ inches.

*Borne.*—Terminal as a spray.

*Color.*—General tonality: Dark red, with little fading. Upper side: Near to from 45A to 46B. Lower side: Near to from 46B. Center: Near to from 45A. Outer petals: Near to from 45A to 46B.

*Keeping quality.*—good.

*Fragrance.*—Slight.

Petals:

*Number.*—About 36 to 37.

*Outer petals.*—Length: About 1⅓ inches. Width: About 1¼ inches.

*Central petals.*—Length: About 1-inch. Width: About 1-inch.

*Texture.*—Smooth.

*Form.*—Fan shaped.

*Appearance.*—Shiny.

Reproductive Organs:

*Stamens.*—Number: About 9. Arrangement: Around the ovary.

*Anthers.*—Length: About 1/9-inch. Color: Near 161C.

*Filaments.*—Length: About 1-inch. Color: Near 155D.

*Pistils.*—Number: About 3. Color: Near 74D.

*Stigma.*—Number: About 3. Color: Near 74D.

*Ovary.*—Shape: Conical, ribbed. Color: Base — green. Body — green. Apex — tan.

*Fertility.*—Male — poor. Female — poor.

I claim:

1. A new and distinct variety of carnation plant, substantially as shown and described.

* * * * *

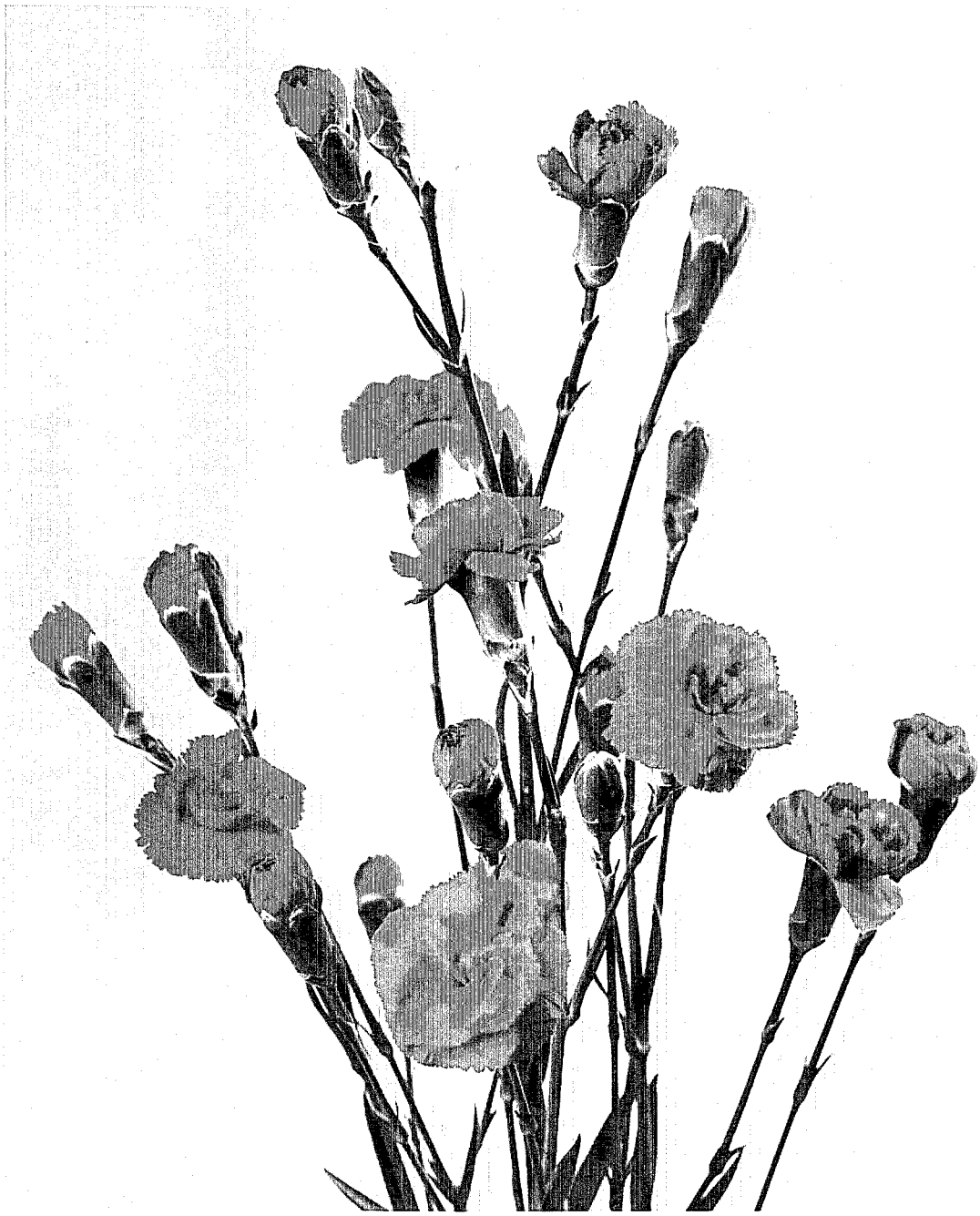

UNITED STATES PATENT AND TRADEMARK OFFICE

CERTIFICATE OF CORRECTION

PATENT NO. : Plant 8,428

DATED : October 19, 1993

INVENTOR(S) : Walter H. Jessel, Jr.

It is certified that error appears in the above-indentified patent and that said Letters Patent is hereby corrected as shown below:

Column 1, line 35, change "which" to -- with --.

Column 1, line 42, change "envirnomental" to -- environmental --.

Signed and Sealed this

Twenty-fourth Day of May, 1994

*Attest:*

Bruce Lehman

BRUCE LEHMAN

*Attesting Officer*

*Commissioner of Patents and Trademarks*